US009804101B2

(12) United States Patent
Deng et al.

(10) Patent No.: US 9,804,101 B2
(45) Date of Patent: Oct. 31, 2017

(54) SYSTEM AND METHOD FOR REDUCING THE BANDWIDTH OF A LASER AND AN INSPECTION SYSTEM AND METHOD USING A LASER

(71) Applicant: KLA-Tencor Corporation, Milpitas, CA (US)

(72) Inventors: Yujun Deng, San Jose, CA (US); Yung-Ho Chuang, Cupertino, CA (US); John Fielden, Los Altos, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 479 days.

(21) Appl. No.: 14/300,227

(22) Filed: Jun. 9, 2014

(65) Prior Publication Data

US 2015/0268176 A1 Sep. 24, 2015

Related U.S. Application Data

(60) Provisional application No. 61/955,792, filed on Mar. 20, 2014.

(51) Int. Cl.
*G01J 1/42* (2006.01)
*G01N 21/95* (2006.01)
*H01S 3/094* (2006.01)
*G01N 21/88* (2006.01)
*G02F 1/39* (2006.01)
(Continued)

(52) U.S. Cl.
CPC ..... *G01N 21/9501* (2013.01); *G01N 21/8806* (2013.01); *G02F 1/39* (2013.01); *H01S 3/094015* (2013.01); *G02F 1/3534* (2013.01); *H01S 3/0078* (2013.01); *H01S 3/0092* (2013.01)

(58) Field of Classification Search
CPC ....... H01S 3/0092; H01S 3/1083; H01S 3/109
See application file for complete search history.

(56) References Cited

U.S. PATENT DOCUMENTS 3,755,704 A 8/1973 Spindt et al.
4,178,561 A 12/1979 Hon et al.
(Continued)

FOREIGN PATENT DOCUMENTS

CN 101702490 5/2010
DE 102007004235 1/2008
(Continued)

OTHER PUBLICATIONS

KLA-Tencor Corporation, U.S. Appl. No. 14/248,045, filed Apr. 8, 2014 and entitled "Passivation of Nonlinear Optical Crystals".
(Continued)

*Primary Examiner* — Kenneth J Malkowski
(74) *Attorney, Agent, or Firm* — Bever, Hoffman & Harms, LLP

(57) ABSTRACT

A DUV laser includes an optical bandwidth filtering device, such as etalon, which is disposed outside of the laser oscillator cavity of the fundamental laser, and which directs one range of wavelengths into one portion of a frequency conversion chain and another range of wavelengths into another portion of the frequency conversion train, thereby reducing the bandwidth of the DUV laser output while maintaining high conversion efficiency in the frequency conversion chain.

12 Claims, 9 Drawing Sheets

(51) Int. Cl.
*H01S 3/00* (2006.01)
*G02F 1/35* (2006.01)

(56) References Cited

U.S. PATENT DOCUMENTS

| | | | |
|---|---|---|---|
| 4,467,189 A | 8/1984 | Tsuchiya | |
| 4,644,221 A | 2/1987 | Gutierrez et al. | |
| 4,710,030 A | 12/1987 | Tauc et al. | |
| 4,853,595 A | 8/1989 | Alfano et al. | |
| 4,999,014 A | 3/1991 | Gold et al. | |
| 5,120,949 A | 6/1992 | Tomasetti | |
| 5,144,630 A | 9/1992 | Lin | |
| 5,189,481 A | 2/1993 | Jann et al. | |
| 5,563,702 A | 10/1996 | Emery et al. | |
| 5,572,598 A | 11/1996 | Wihl et al. | |
| 5,742,626 A * | 4/1998 | Mead | G02F 1/37 359/326 |
| 5,760,809 A | 6/1998 | Malhotra et al. | |
| 5,760,899 A | 6/1998 | Eismann | |
| 5,825,562 A | 10/1998 | Lai et al. | |
| 5,898,717 A * | 4/1999 | Yin | H01S 3/109 372/22 |
| 5,999,310 A | 12/1999 | Shafer et al. | |
| 6,064,759 A | 5/2000 | Buckley et al. | |
| 6,201,257 B1 | 3/2001 | Stettner et al. | |
| 6,201,601 B1 | 3/2001 | Vaez-Iravani et al. | |
| 6,212,310 B1 | 4/2001 | Waarts et al. | |
| 6,220,914 B1 | 4/2001 | Lee et al. | |
| 6,249,371 B1 | 6/2001 | Masuda et al. | |
| 6,271,916 B1 | 8/2001 | Marxer et al. | |
| 6,285,018 B1 | 9/2001 | Aebi et al. | |
| 6,373,869 B1 | 4/2002 | Jacob | |
| 6,498,801 B1 | 12/2002 | Dudelzak et al. | |
| 6,577,782 B1 | 6/2003 | Leaird et al. | |
| 6,590,698 B1 | 7/2003 | Ohtsuki et al. | |
| 6,608,676 B1 | 8/2003 | Zhao et al. | |
| 6,693,930 B1 | 2/2004 | Chuang et al. | |
| 6,734,968 B1 | 5/2004 | Wang et al. | |
| 6,816,520 B1 | 11/2004 | Tulloch et al. | |
| 6,859,335 B1 | 2/2005 | Lai et al. | |
| 6,888,855 B1 | 5/2005 | Kopf | |
| 7,098,992 B2 | 8/2006 | Ohtsuki et al. | |
| 7,136,402 B1 | 11/2006 | Ohtsuki | |
| 7,187,500 B2 | 3/2007 | Chuang et al. | |
| 7,313,155 B1 | 12/2007 | Mu | |
| 7,339,961 B2 | 3/2008 | Tokuhisa et al. | |
| 7,345,825 B2 | 3/2008 | Chuang et al. | |
| 7,352,457 B2 | 4/2008 | Kvamme et al. | |
| 7,449,673 B2 | 11/2008 | Chuang et al. | |
| 7,463,657 B2 | 12/2008 | Spinelli et al. | |
| 7,471,705 B2 | 12/2008 | Gerstenberger et al. | |
| 7,525,649 B1 | 4/2009 | Leong et al. | |
| 7,528,342 B2 | 5/2009 | Deshi | |
| 7,528,943 B2 | 5/2009 | Brown et al. | |
| 7,586,108 B2 | 9/2009 | Nihtianov et al. | |
| 7,593,437 B2 | 9/2009 | Staroudoumov et al. | |
| 7,593,440 B2 | 9/2009 | Spinelli et al. | |
| 7,609,309 B2 | 10/2009 | Brown et al. | |
| 7,623,557 B2 | 11/2009 | Tokuhisa et al. | |
| 7,627,007 B1 | 12/2009 | Armstrong et al. | |
| 7,643,529 B2 | 1/2010 | Brown et al. | |
| 7,667,841 B2 | 2/2010 | Opsal | |
| 7,715,459 B2 | 5/2010 | Brown et al. | |
| 7,813,406 B1 | 10/2010 | Nguyen et al. | |
| 7,822,092 B2 | 10/2010 | Ershov et al. | |
| 7,875,948 B2 | 1/2011 | Hynecek et al. | |
| 7,920,616 B2 | 4/2011 | Brown et al. | |
| 7,952,633 B2 | 5/2011 | Brown et al. | |
| 7,957,066 B2 | 6/2011 | Armstrong et al. | |
| 7,999,342 B2 | 8/2011 | Hsu et al. | |
| 8,017,427 B2 | 9/2011 | Manabe | |
| 8,208,505 B2 | 6/2012 | Dantus et al. | |
| 8,238,647 B2 | 8/2012 | Ben-Yishay et al. | |
| 8,298,335 B2 | 10/2012 | Armstrong | |
| 8,309,443 B2 | 11/2012 | Tanaka et al. | |
| 8,319,960 B2 | 11/2012 | Aiko et al. | |
| 8,391,660 B2 | 3/2013 | Islam | |
| 8,503,068 B2 | 8/2013 | Sakuma | |
| 8,514,587 B2 | 8/2013 | Zhang et al. | |
| 8,629,384 B1 | 1/2014 | Biellak et al. | |
| 8,686,331 B2 | 4/2014 | Armstrong | |
| 8,755,417 B1 | 6/2014 | Dribinski | |
| 8,873,596 B2 | 10/2014 | Dribinski | |
| 8,891,079 B2 | 11/2014 | Zhao et al. | |
| 8,929,406 B2 | 1/2015 | Chuang et al. | |
| 2001/0000977 A1 | 5/2001 | Vaez-Iravani et al. | |
| 2002/0109110 A1 | 8/2002 | Some et al. | |
| 2002/0114553 A1 | 8/2002 | Mead et al. | |
| 2002/0191834 A1 | 12/2002 | Fishbaine | |
| 2003/0043876 A1 | 3/2003 | Lublin et al. | |
| 2003/0147128 A1 | 8/2003 | Shafer et al. | |
| 2003/0161374 A1 | 8/2003 | Lokai | |
| 2004/0080741 A1 | 4/2004 | Marxer et al. | |
| 2004/0095573 A1 | 5/2004 | Tsai et al. | |
| 2005/0041702 A1 | 2/2005 | Fermann et al. | |
| 2005/0110988 A1 | 5/2005 | Nishiyama et al. | |
| 2005/0111081 A1 | 5/2005 | Shafer et al. | |
| 2005/0122021 A1 | 6/2005 | Smith et al. | |
| 2005/0128473 A1 | 6/2005 | Karpol et al. | |
| 2005/0157382 A1 | 7/2005 | Kafka et al. | |
| 2005/0190452 A1 | 9/2005 | Govorkov et al. | |
| 2005/0254049 A1 | 11/2005 | Zhao | |
| 2005/0254065 A1 | 11/2005 | Stokowski | |
| 2006/0038984 A9 | 2/2006 | Vaez-Iravani et al. | |
| 2006/0054778 A1 | 3/2006 | Suhling | |
| 2006/0126682 A1 | 6/2006 | Rodin et al. | |
| 2006/0171036 A1 | 8/2006 | Govorkov et al. | |
| 2006/0171656 A1 | 8/2006 | Adachi et al. | |
| 2006/0239535 A1 | 10/2006 | Takada | |
| 2006/0291862 A1 | 12/2006 | Kawai | |
| 2007/0002465 A1 | 1/2007 | Chuang et al. | |
| 2007/0047600 A1 | 3/2007 | Luo et al. | |
| 2007/0096648 A1 | 5/2007 | Nakajima et al. | |
| 2007/0103769 A1 | 5/2007 | Kuwabara | |
| 2007/0121107 A1 | 5/2007 | Tsai et al. | |
| 2007/0146693 A1 | 6/2007 | Brown et al. | |
| 2007/0188744 A1 | 8/2007 | Leslie et al. | |
| 2007/0211773 A1 | 9/2007 | Gerstenberger et al. | |
| 2007/0263680 A1 | 11/2007 | Staroudoumov et al. | |
| 2007/0291810 A1 | 12/2007 | Luo et al. | |
| 2008/0182092 A1 | 7/2008 | Bondokov et al. | |
| 2008/0186476 A1 | 8/2008 | Kusunose | |
| 2008/0204737 A1 | 8/2008 | Ogawa | |
| 2009/0084989 A1 | 4/2009 | Imai | |
| 2009/0108207 A1 | 4/2009 | Liu | |
| 2009/0128912 A1 | 5/2009 | Okada | |
| 2009/0180176 A1 | 7/2009 | Armstrong et al. | |
| 2009/0185583 A1 | 7/2009 | Kuksenkov et al. | |
| 2009/0185588 A1 | 7/2009 | Munroe | |
| 2009/0296755 A1 | 12/2009 | Brown et al. | |
| 2009/0324234 A1* | 12/2009 | Kashima | H04B 10/27 398/92 |
| 2010/0103409 A1 | 4/2010 | Ohshima et al. | |
| 2010/0108913 A1 | 5/2010 | Ershov et al. | |
| 2010/0188655 A1 | 7/2010 | Brown et al. | |
| 2010/0301437 A1 | 12/2010 | Brown et al. | |
| 2011/0062127 A1 | 3/2011 | Gu et al. | |
| 2011/0073982 A1 | 3/2011 | Armstrong et al. | |
| 2011/0085149 A1 | 4/2011 | Nathan | |
| 2011/0101219 A1 | 5/2011 | Uchiyama et al. | |
| 2011/0134944 A1 | 6/2011 | Kaneda et al. | |
| 2011/0222565 A1 | 9/2011 | Horain et al. | |
| 2011/0228263 A1 | 9/2011 | Chuang et al. | |
| 2011/0279819 A1 | 11/2011 | Chuang et al. | |
| 2012/0026578 A1 | 2/2012 | Sakuma | |
| 2012/0033291 A1 | 2/2012 | Kneip | |
| 2012/0092657 A1 | 4/2012 | Shibata | |
| 2012/0113995 A1 | 5/2012 | Armstrong | |
| 2012/0120481 A1 | 5/2012 | Armstrong | |
| 2012/0137909 A1 | 6/2012 | Hawes et al. | |
| 2012/0160993 A1 | 6/2012 | Nevet et al. | |
| 2012/0314286 A1 | 12/2012 | Chuang et al. | |
| 2013/0009069 A1 | 1/2013 | Okada | |
| 2013/0016346 A1 | 1/2013 | Romanovsky et al. | |

(56) References Cited

U.S. PATENT DOCUMENTS

| | | |
|---|---|---|
| 2013/0020491 A1 | 1/2013 | Mazzillo |
| 2013/0021602 A1 | 1/2013 | Dribinski et al. |
| 2013/0064259 A1 | 3/2013 | Wakabayashi et al. |
| 2013/0077086 A1 | 3/2013 | Chuang et al. |
| 2013/0082241 A1 | 4/2013 | Kub et al. |
| 2013/0088706 A1 | 4/2013 | Chuang et al. |
| 2013/0126705 A1 | 5/2013 | Maleev |
| 2013/0169957 A1 | 7/2013 | Wolf et al. |
| 2013/0176552 A1 | 7/2013 | Brown et al. |
| 2013/0194445 A1 | 8/2013 | Brown et al. |
| 2013/0264481 A1 | 10/2013 | Chern et al. |
| 2013/0313440 A1 | 11/2013 | Chuang et al. |
| 2013/0336574 A1 | 12/2013 | Nasser-Ghodsi et al. |
| 2014/0016655 A1 | 1/2014 | Armstrong |
| 2014/0034816 A1 | 2/2014 | Chuang et al. |
| 2014/0050234 A1 | 2/2014 | Ter-Mikirtychev |
| 2014/0071520 A1 | 3/2014 | Armstrong |
| 2014/0111799 A1 | 4/2014 | Lei et al. |
| 2014/0133503 A1 | 5/2014 | Peng et al. |
| 2014/0153596 A1 | 6/2014 | Chuang et al. |
| 2014/0158864 A1 | 6/2014 | Brown et al. |
| 2014/0204963 A1 | 7/2014 | Chuang et al. |
| 2014/0226140 A1 | 8/2014 | Chuang et al. |
| 2014/0291493 A1 | 10/2014 | Chuang et al. |
| 2014/0305367 A1 | 10/2014 | Chuang et al. |
| 2015/0007765 A1 | 1/2015 | Dribinski |
| 2015/0177159 A1 | 6/2015 | Brown et al. |
| 2015/0200216 A1 | 7/2015 | Muramatsu et al. |
| 2015/0275393 A1 | 10/2015 | Bondokov et al. |
| 2015/0294998 A1 | 10/2015 | Nihtianov |
| 2015/0372446 A1 | 12/2015 | Chuang et al. |

FOREIGN PATENT DOCUMENTS

| | | |
|---|---|---|
| EP | 0532927 | 3/1993 |
| EP | 0746871 B1 | 5/2000 |
| EP | 0602983 B1 | 6/2000 |
| EP | 1194804 B1 | 7/2003 |
| EP | 1939917 A2 | 7/2008 |
| EP | 2013951 | 1/2009 |
| JP | H0511287 A | 1/1993 |
| JP | 2002-258339 A | 9/2002 |
| JP | 2003043533 A | 2/2003 |
| JP | 2006-60162 A | 3/2006 |
| JP | 2006-186046 A | 7/2006 |
| JP | 200786108 | 4/2007 |
| JP | 2007-206452 A | 8/2007 |
| JP | 2007249092 A | 9/2007 |
| JP | 2007298932 A | 11/2007 |
| JP | 2009-145791 | 7/2009 |
| JP | 2010-54547 | 3/2010 |
| JP | 2010-256784 | 11/2010 |
| JP | 2011-23532 A | 2/2011 |
| JP | 2011-128330 A | 8/2011 |
| JP | 2012-098103 A | 5/2012 |
| KR | 1020000034461 A | 6/2000 |
| KR | 1020100025297 A | 3/2010 |
| WO | 9532518 A1 | 11/1995 |
| WO | 9617372 A1 | 6/1996 |
| WO | 00/14834 A1 | 3/2000 |
| WO | 03/069263 | 8/2003 |
| WO | 2005/022705 A2 | 3/2005 |
| WO | 2009/082460 | 7/2009 |
| WO | 2010/037106 | 4/2010 |
| WO | 2011/064059 A1 | 6/2011 |
| WO | 2012/154468 | 11/2012 |
| WO | 2013/015940 A1 | 1/2013 |
| WO | 2013006867 A1 | 1/2013 |
| WO | 2014067754 A2 | 5/2014 |

OTHER PUBLICATIONS

KLA-Tencor Corporation, U.S. Appl. No. 62/059,368, filed Oct. 3, 2014 and entitled "183nm Laser and Inspection System".

Raoult, F. et al., "Efficient generation of narrow-bandwidth picosecond pulses by frequency doubling of femtosecond chirped pulses", Jul. 15, 1998 / ol. 23, No. 14 / Optics Letters, pp. 1117-1119.

KLA-Tencor Corpoation, U.S. Appl. No. 14/210,355, filed Mar. 13, 2014 and entitled "193nm Laser and an Inspection System Using a 193nm Laser".

KLA-Tencor Corporation; PCT International Search Report dated Dec. 29, 2015 for Application No. PCT/US2015/051538, 3 pages.

Huang, Qiyu et al., "Back-Side Illuminated Photogate CMOS Active Pixel Sensor Structure With Improved Short Wavelength Response", IEEE Sensors Journal, vol. 11, No. 9, Sep. 2011, 5 pages.

Itzler, Mark et al., "InP-based Geiger-mode avalanche photodiode arrays for three-dimensional imaging at 1.06 μm", Proceedings of SPIE, vol. 7320 (2000), 12 pages.

Niclass, Cristiano et al., "Design and Characterization of a CMOS 3-D Image Sensor Based on Single Photon Avalanche Diodes", IEEE Journal of Solid-State Circuits, vol. 40, No. 9, Sep. 2005, 8 pages.

Paetzel, Rainer et al., "Activation of Silicon Wafer by Excimer Laser" 18th IEEE Conf. Advanced Thermal processing of Semiconductors—RTP 2010, 5 pages.

Stevanovic, Nenad et al., "A CMOS Image Sensor for High-Speed Imaging", 2000 IEEE Int'l. Conference Solid-State Circuits, 3 pages.

Dulinski, Wojciech et al., "Tests of a backside illuminated monolithic CMOS pixel sensor in an HPD set-up", Nuclear Instruments and Methods in Physics Research A 546 (2005) 274-280, 7 pages.

Sarubbi, F et al, "Pure boron-doped photodiodes: a solution for radiation detection in EUV lithography", Proceedings of the 38th EP Solid-State Device Research Conf., Edinburgh Int'l. Conf. Centre, Endiburgh, Scotland, UK, Sep. 15-19, 2008, Piscataway, NJ: IEEE, US, pp. 278-281.

Fu, Xiaoqian, "Higher Quantum Efficiency by Optimizing GaN Photocathode Structure", 978-1-4244-6644-3/10/ © 2010 IEEE, pp. 234-235.

Sakic, Agata, "Boron-layer silicon photodiodes for high-efficiency low-energy electron detection", Solid-State Electronics 65-66 (2011), pp. 38-44.

Omatsu, Takashige et al., "High repetition rate Q-switching performance in transversely diode-pumped Nd doped mixed gadolinium yttrium vanadate bounce laser", Optics Express vol. 14, Issue 7, pp. 2727-2734, Apr. 3, 2006.

Armstrong, Carter M.The Quest for the Ultimate Vacuum Tube, Spectrum IEEE, Dec. 2015, 4 pgs.

Ding, MengField Emission from Silicon, MIT 2001, 277 pgs.

Fanton et al, Multiparameter Measurements of Thin Film . . . , Journal of Applied Physics, vol. 73, No. 11, p. 7035 (1993).

Field Emitter Review, 7 pgs in Japanese.

Fowler, R. H., et al, Electron Emission in Intense Electric Fields, Mar. 31, 1928, 9 pgs.

Koike, AkifumiField Emitter Equipped With a Suppressor to Control Emission Angel, IEEE Electron Device Letters, vol. 34, No. 5, May 2013, 3 pgs.

Nagao, Masayoshi, Cathode Technologies for Field Emission Displays, IEEJ Trans 2006; 1:171-178, 8 pgs.

Nagao, MasayoshiFabrication of a Field Emitter Array with a Built-In Einzel Lens, JJAP 48 (2008) 06FK02, 4 pgs.

Neo, YoichiroElectron Optical Properties of Microcolumn with Field Emitter, JJAP 52 (2013) 036603, 5 pgs.

Rakhshandehroo, M.R. et al, Fabrication of a self-aligned silicon field emission . . . , JVSTB, 16, 765 (1998); doi: 10.1116/1,589900, 6 pgs.

Rakhshandehroo, M.R. et al, Field emission from gated Si emitter tips with precise . . . , JVSTB, 15, 2777 (1997); doi: 10.1116/1.589726, 6 pgs.

Sato, T., et al, Fabrication and characterization of HfC coated . . . , J. Vac. Sci. Technol. B 2194), published Jul. 31, 2003, 5 pgs.

Serbun Pavel et al, Stable field emission of single B-doped . . . , JVSTB, 31, 02B101 (2013); doi: 10.1116/1.4765088, 7 pgs.

Utsumi, TakaoVacuum Microelectrnoics: What's New and Exciting, IEEE vol. 38, No. 10, Oct. 1991, 8 pgs.

(56) References Cited

OTHER PUBLICATIONS

Dianov et al. "Bi-doped fiber lasers: new type of high-power radiation sources", Conference on Lasers and Electro-Optics, May 6-11, 2007, 2 pages.

Kalita et al. "Multi-watts narrow-linewidth all fiber Yb-doped laser operating at 1179 nm", Optics Express, 18 (6), pp. 5920-5925 (2010).

Kashiwagi et al. "Over 10W output linearly-polarized single-stage fiber laser oscillating above 1160 nm using Yb-doped polarization-maintaining solid photonic bandgap fiber", IEEE Journal of Quantum Electronics, 47 (8), pp. 1136-1141 (2011).

Mead et al. "Solid-state lasers for 193-nm photolithography", Proc. SPIE 3051, Optical Microlithography X, pp. 882-889 (Jul. 7, 1997).

Saikawa et al. "52 mJ narrow-bandwidth degenerated optical parametric system with a large-aperture periodically poled $MgO:LiNbO_3$ device", Optics Letters, 31 (#21), 3149-3151 (2006).

Sakuma et al. "High power, narrowband, DUV laser source by frequency mixing in CLBO", Advanced High-Power Lasers and Applications, Nov. 2000, pp. 7-14, Ushio Inc.

Sakuma et al. "True CW 193.4-nm light generation based on frequency conversion of fiber amplifiers", Optics Express 19 (#16), 15020-15025 (2011).

Sasaki et al. "Progress in the growth of a $CsLiB_6O_{10}$ crystal and its application to ultraviolet light generation", Optical Materials, vol. 23, 343-351 (2003).

Shirakawa et al. "High-power Yb-doped photonic bandgap fiber amplifier at 1150-1200nm", Optics Express 17 (2), 447-454 (2009).

Ter-Mikirtychev et al. "Tunable $LiF:F_2$-color center laser with an intracavity integrated-optic output coupler", Journal of Lightwave Technology, 14 (10), 2353-2355 (1996).

Yoo et al. "Excited state absorption measurement in bismuth-doped silicate fibers for use in 1160 nm fiber laser", 3rd EPS-QEOD Europhoton Conference, Paris, France, Aug. 31-Sep. 5, 2008, 1 page.

Zavartsev et al. "High efficient diode pumped mixed vanadate crystal $Nd:Gd_{0.7}Y_{0.3}VO_4$ laser", International Conference on Lasers, Applications, and Technologies 2007: Advanced Lasers and Systems, Valentin A. Orlovich et al. ed., Proc. of SPIE vol. 6731, 67311P (2007), 5 pages.

File history for U.S. Appl. No. 11/735,967, filed Apr. 16, 2007 by Vladimir L. Dribinski et al.

RP Photonics, RP Photonics Encyclopedia, "Chirp", Publication date unknown, Available online: http://www.rp-photonics.com/chirp.html.

Agrawal, Govind P. "Nonlinear Fiber Optics," Academic Press, 4th ed., 2007, pp. 54-59.

International Search Report and Written Opinion dated May 13, 2014 for PCT/US2014/012902, filed Jan. 24, 2014 in the name of KLA-Tencor Corporation.

Herriott et al.: "Off-Axis Paths in Spherical Mirror Interferometers", Applied Optics 3, #4, pp. 523-526 (1964).

Herriott et al.: "Folded Optical Delay Lines", Applied Optics 4, #8, pp. 883-889 (1965).

White, John U.: "Long Optical Paths of Large Aperture", Journal of the Optical Society of America 32, #5, pp. 285-288 (1942).

International Search Report and Written Opinion dated Mar. 19, 2014 for PCT/US2013/072774 filed Dec. 3, 2013 in the name of KLA-Tencor Corporation (14 pages).

International Search Report and Written Opinion dated Jul. 11, 2014 for PCT/US2014/030989, filed Mar. 18, 2014 in the name of KLA-Tencor Corporation.

International Search Report and Written Opinion dated May 20, 2014 for PCT/US2014/016198, filed Feb. 13, 2014 in the name of KLA-Tencor Corporation.

\* cited by examiner

SYSTEM AND METHOD FOR REDUCING THE BANDWIDTH OF A LASER AND AN INSPECTION SYSTEM AND METHOD USING A LASER

PRIORITY APPLICATION

The present application claims priority to U.S. Provisional Patent Application 61/955,792, entitled "A System and Method for Reducing the Bandwidth of a Laser and an Inspection System and Method Using a Laser", filed on Mar. 20, 2014, and incorporated by reference herein.

RELATED APPLICATIONS

The present application is related to U.S. Provisional Patent Application 61/756,209, entitled "193 nm Laser Using OPO and an Inspection System Using a 193 nm Laser", filed on Jan. 24, 2013, U.S. patent application Ser. No. 14/158,615, entitled "193 nm Laser and Inspection System", filed on Jan. 17, 2014, U.S. patent application Ser. No. 13/797,939, entitled "Solid-State Laser and Inspection System Using 193 nm Laser", filed on Mar. 12, 2013, U.S. Provisional Patent Application 61/764,441, entitled "193 nm Laser and an Inspection System Using a 193 nm Laser", filed on Feb. 13, 2013, U.S. patent application Ser. No. 14/170,384, entitled "193 nm Laser and Inspection System", filed on Jan. 31, 2014, U.S. Provisional Patent Application 61/733,858, entitled "Semiconductor Inspection and Metrology System Using Laser Pulse Multiplier", filed on Dec. 5, 2012, and U.S. patent application Ser. No. 13/711,593, entitled "Semiconductor Inspection and Metrology System Using Laser Pulse Multiplier", filed on Dec. 11, 2012. These related applications are incorporated by reference herein.

BACKGROUND OF THE DISCLOSURE

Field of the Disclosure

The present application relates to lasers suitable for generating radiation at deep UV (DUV) and vacuum UV (VUV) wavelengths, and to methods for generating laser light at DUV and VUV wavelengths. In particular, the present application relates to systems and methods for reducing and controlling the spectral bandwidth of DUV and VUV lasers. The lasers described herein are particularly suitable for use in inspection systems including those used to inspect photomasks, reticles, and semiconductor wafers.

Related Art

The integrated circuit industry requires inspection tools with increasingly higher sensitivity to detect ever smaller defects and particles whose sizes may be 100 nm or smaller. Furthermore, these inspection tools must operate at high speed to inspect a large fraction or even 100% of the area of a photomask, reticle or wafer in a short period of time, e.g. one hour or less.

Generally, short wavelengths such as DUV and VUV wavelengths have higher sensitivity for detecting small defects compared with longer wavelengths. Inspection of a photomask or a reticle is preferably done using the same wavelength as the lithography used when printing from the photomask or reticle. Currently, a wavelength of substantially 193.4 nm is used for the most critical lithography steps and a wavelength of substantially 248 nm is used for less critical lithography steps.

High-speed inspection requires high power lasers to illuminate the samples being inspected with high intensity to detect the small amount of light scattered from small particles or defects or allow detection of small changes in reflectivity due to defects in the pattern. The required laser power levels may range from approximately 100 mW for the inspection of photomasks and reticles up to more than 10 W for the detection of small particles and imperfections on a bare silicon wafer.

Typically, inspection in the semiconductor industry requires lasers with very narrow bandwidth. Such inspection systems usually use an objective lens with a large field of view (typically from a few hundred microns to a few mm in dimensions) to allow imaging of a large area at high inspection speeds. An objective lens with low distortions and a large field of view is expensive and complex. Requiring that objective lens to operate over a large bandwidth (such as more than a few tens of pm) significantly increases the cost and complexity. DUV lasers with bandwidths of approximately 20 pm or less are very desirable for inspection applications in the semiconductor industry.

DUV lasers are known in the art. U.S. Pat. No. 5,144,630 entitled "Multiwave Solid State Laser Using Frequency Conversion Techniques" that issued on Sep. 1, 1992 to Lin, and U.S. Pat. No. 5,742,626, entitled "Ultraviolet Solid State Laser Method Of Using Same And Laser Surgery Apparatus", issued on Apr. 21, 1998 to Mead et al. describe exemplary DUV lasers. In these lasers, fourth and fifth harmonics are generated from a pulsed fundamental infra-red laser operating at a wavelength near 1064 nm, thereby resulting in wavelengths of approximately 266 nm and 213 nm. Lin and Mead also teach generating an infra-red wavelength longer than 1064 nm from the fundamental laser using an optical parametric oscillator (OPO).

The output bandwidth of a laser oscillator is determined by its intra-cavity dynamics. In prior art pulsed lasers, to further reduce laser bandwidth, various bandwidth limiting devices, such as an etalon, a birefringent filter, or an optical grating, have been incorporated into a laser cavity. Because all of these approaches are invasive, they inevitably introduce detrimental effects to the lasers. These detrimental effects include extra power losses and greater complexity, which often lead to lower laser efficiency, poor thermal stability, tighter misalignment sensitivity, and longer laser system warm-up time. Furthermore, because intra-cavity beam size is often small and predetermined by laser cavity design, and intra-cavity laser power density is normally much higher than laser output power, these intra-cavity components are much more susceptible to damage.

In prior art pulsed DUV lasers, the bandwidth of the DUV output depends directly on the bandwidth of the fundamental infra-red laser. That is, the broader the bandwidth of the fundamental laser, the broader the DUV output bandwidth. Reducing the bandwidth of a laser requires redesigning the laser oscillator cavity. Because the cavity may control many properties of the laser including bandwidth, repetition rate, as well as average and peak powers, redesigning the cavity to reduce the bandwidth while maintaining the other laser parameters may be a complex and time consuming task. Furthermore, achieving a specific DUV laser bandwidth specification may not be possible using a readily available infra-red fundamental laser.

It is well-known that a chirp stretches the length of a laser pulse and reduces its peak power (see, for example, http://www.rp-photonics.com/chirp.html). As non-linear conversion efficiency scales with peak power, a lower peak power would reduce the overall conversion efficiency, thereby limiting the maximum UV power generated from a laser system. Therefore, for a given required bandwidth, close to transform-limited (also called "chirp-free") pulses are desirable for high non-linear conversion efficiency. However, because of laser intra-cavity dynamics, such as dispersion, spatial-hole burning (SHB), gain saturation, and non-linearity, pulses generated from lasers are often chirped.

Therefore, a need arises for DUV laser overcoming some, or all, of the above disadvantages. In particular, a need arises for a means of reducing or controlling the bandwidth of a DUV laser.

SUMMARY OF THE DISCLOSURE

A DUV laser for providing optimized bandwidth control is described. This DUV laser includes a fundamental laser, a frequency conversion module, a frequency mixing module, and an optical bandwidth filtering device. The fundamental laser generates a fundamental wavelength with a fundamental wavelength bandwidth. The optical bandwidth filtering device is positioned to receive the fundamental wavelength, and selects first and second portions from the fundamental wavelength such that the second portion comprises a narrower range of wavelengths within the fundamental wavelength bandwidth than the first portion. The frequency conversion module converts the first portion of the fundamental wavelength to provide "signal light" having a second wavelength, and the frequency mixing module mixes the second wavelength with the second portion of the fundamental wavelength to generate a sum (output) wavelength. By utilizing the optical bandwidth filtering device to select the narrower second portion, the present invention reduces system costs by facilitating the use of fundamental lasers having a wide range of fundamental wavelength bandwidths (i.e., the need for expensive "custom-built" fundamental lasers having a specific narrow fundamental wavelength bandwidth is avoided). In addition, by utilizing the frequency conversion module to extract signal light having the usable second wavelength from the broad "rejected" first portion of the fundamental frequency, and to direct the signal light into the frequency mixing module for mixing with the second portion, the present invention also minimizes energy loss by effectively "recycling" usable portions of the first ("rejected") portion of the fundamental frequency. The resulting sum (output) wavelength is therefore efficiently produced from a broad fundamental wavelength bandwidth having a much narrower wavelength bandwidth than could be produced using conventional techniques (e.g., harmonic conversion and frequency mixing).

In another embodiment, the DUV laser includes a fundamental laser, a frequency conversion module, a harmonic conversion module, a frequency mixing module, and an optical bandwidth filtering device. The fundamental laser generates a fundamental wavelength with a fundamental wavelength bandwidth. The frequency conversion module converts a first portion of the fundamental wavelength to a second wavelength. The harmonic conversion module generates a harmonic wavelength from a second portion of the fundamental wavelength. The frequency mixing module mixes the second wavelength with the harmonic wavelength to generate a sum wavelength. The optical bandwidth filtering device selects the first and second portions from the fundamental wavelength such that the second portion comprises a narrower range of wavelengths within the fundamental wavelength bandwidth than the first portion.

In yet another embodiment, the DUV laser includes a fundamental laser, a frequency conversion module, a harmonic conversion module, a frequency mixing module, and an optical bandwidth filtering device. The fundamental laser generates a fundamental wavelength with a fundamental wavelength bandwidth. The frequency conversion module converts a first portion of the fundamental wavelength to a second wavelength. The harmonic conversion module generates a harmonic wavelength from the second wavelength. The frequency mixing module mixes the harmonic wavelength with a second portion of the fundamental wavelength to generate a sum wavelength. The optical bandwidth filtering device selects the first and second portions from the fundamental wavelength such that the second portion comprises a narrower range of wavelengths within the fundamental wavelength bandwidth than the first portion.

According to an aspect of the invention, the optical bandwidth filtering device is positioned outside of the laser oscillator cavity of the fundamental laser. The optical bandwidth filtering device may include at least one device selected from a group consisting of an etalon, an optical dielectric filter, a volume Bragg grating, a birefringence filter, and an optical grating. The frequency conversion module may include at least one device selected from a group consisting of an optical parametric oscillator (GPO), an optical parametric amplifier (OPA), and a Raman amplifier. The second wavelength may be generated as signal light from the OPO or the OPA. In one embodiment, the fundamental laser comprises a diode laser generating a wavelength of approximately 405 nm or shorter. In another embodiment, the fundamental laser may comprise a fiber laser, a neodymium-doped yttrium aluminum garnet (Nd:YAG) laser, or a Nd-doped vanadate laser. In one embodiment, the sum wavelength is approximately equal to 193 nm. In another embodiment the sum wavelength is approximately equal to 184 nm.

A method of generating deep UV laser radiation is described. In one embodiment, the method includes generating a fundamental laser light having a fundamental wavelength and a fundamental wavelength bandwidth, converting a first portion of the fundamental wavelength to a second wavelength, generating a harmonic wavelength from a second portion of the fundamental wavelength, and summing the second wavelength and the harmonic wavelength to generate an output wavelength. Notably, the second portion of the fundamental wavelength comprises a narrower range of wavelengths within the fundamental wavelength bandwidth than the first portion.

Another method of generating deep UV laser radiation is described. In one embodiment, this method includes generating a fundamental laser light having a fundamental wavelength and a fundamental wavelength bandwidth, converting a first portion of the fundamental wavelength to a second wavelength, and summing the second wavelength and a second portion of the harmonic wavelength to generate an output wavelength. Notably, the second portion of the fundamental wavelength comprises a narrower range of wavelengths within the fundamental wavelength bandwidth than the first portion.

Yet another method of generating deep UV laser radiation is described. In one embodiment, this method includes generating a fundamental laser light having a fundamental wavelength and a fundamental wavelength bandwidth, converting a first portion of the fundamental wavelength to a second wavelength, generating a harmonic wavelength from the second wavelength, and summing a second portion of the fundamental wavelength and the harmonic wavelength to generate an output wavelength. Notably, the second portion of the fundamental wavelength comprises a narrower range of wavelengths within the fundamental wavelength bandwidth than the first portion.

With respect to these methods, selecting of the first and second portions may be performed by at least one of an etalon, an optical dielectric filter, a volume Bragg grating, a birefringence filter, or an optical grating. Notably, such optical bandwidth filtering devices, in effect, direct one range of wavelengths into one portion of a frequency conversion chain and another range of wavelengths into another portion of the frequency conversion train, thereby substantially reducing the power loss compared with lasers that use the optical bandwidth filtering devices to reduce the bandwidth by simply rejecting unwanted wavelengths. Furthermore, by placing the bandwidth narrowing devices outside the laser cavity, some or all of the detrimental effects of intra-cavity bandwidth-controlling devices can be avoided. Laser parameters other than the bandwidth can be largely maintained without redesigning the laser oscillator cavity. Converting the first portion of the fundamental wavelength to the second wavelength may be performed by an OPO, an OPA, or a Raman amplifier. Generating the fundamental laser light may be performed by one of diode laser, a Nd:YAG laser, an Nd-doped vanadate laser, and an Yb-doped fiber laser.

An exemplary inspection system is described. This inspection system includes an illumination source, optics, and a detector. The illumination source includes a DUV laser that generates DUV radiation of a desired wavelength and bandwidth. The DUV laser includes an optical bandwidth filtering device, e.g. an etalon, that directs one range of wavelengths into one portion of a frequency conversion chain and another range of wavelengths into another portion of the frequency conversion train. The optics are configured to direct and focus radiation from the illumination source onto a sample. The sample is supported by a stage, which moves relative to the optics during the inspection. The detector is configured to receive reflected or scattered light from the sample, wherein the optics are further configured to collect, direct, and focus the reflected or scattered light onto the detector. The detector includes one or more image sensors. At least one image sensor may be a time delay integration (TDI) sensor.

The exemplary inspection system may include one or more illumination paths that illuminate the sample from different angles of incidence and/or different azimuth angles and/or with different wavelengths and/or polarization states. The exemplary inspection system may include one or more collection paths that collect light reflected or scattered by the sample in different directions and/or are sensitive to different wavelengths and/or to different polarization states. The exemplary inspection system may include a TDI sensor with readout circuits on two sides that are used to read out two different signals simultaneously. The exemplary inspection system may include an electron-bombarded image or an avalanche image sensor.

An exemplary method for controlling the bandwidth of a laser and, at the same time, reducing its chirp is described. A bandwidth controlling device is placed outside the laser oscillator cavity. Under certain circumstances, after bandwidth filtering, a chirped pulse can be converted to a closer-to-transform-limited pulse with narrower bandwidth and shorter pulse length. This is highly desirable for higher conversion efficiency in nonlinear frequency conversion.

DETAILED DESCRIPTION OF THE DRAWINGS

Figure 1:
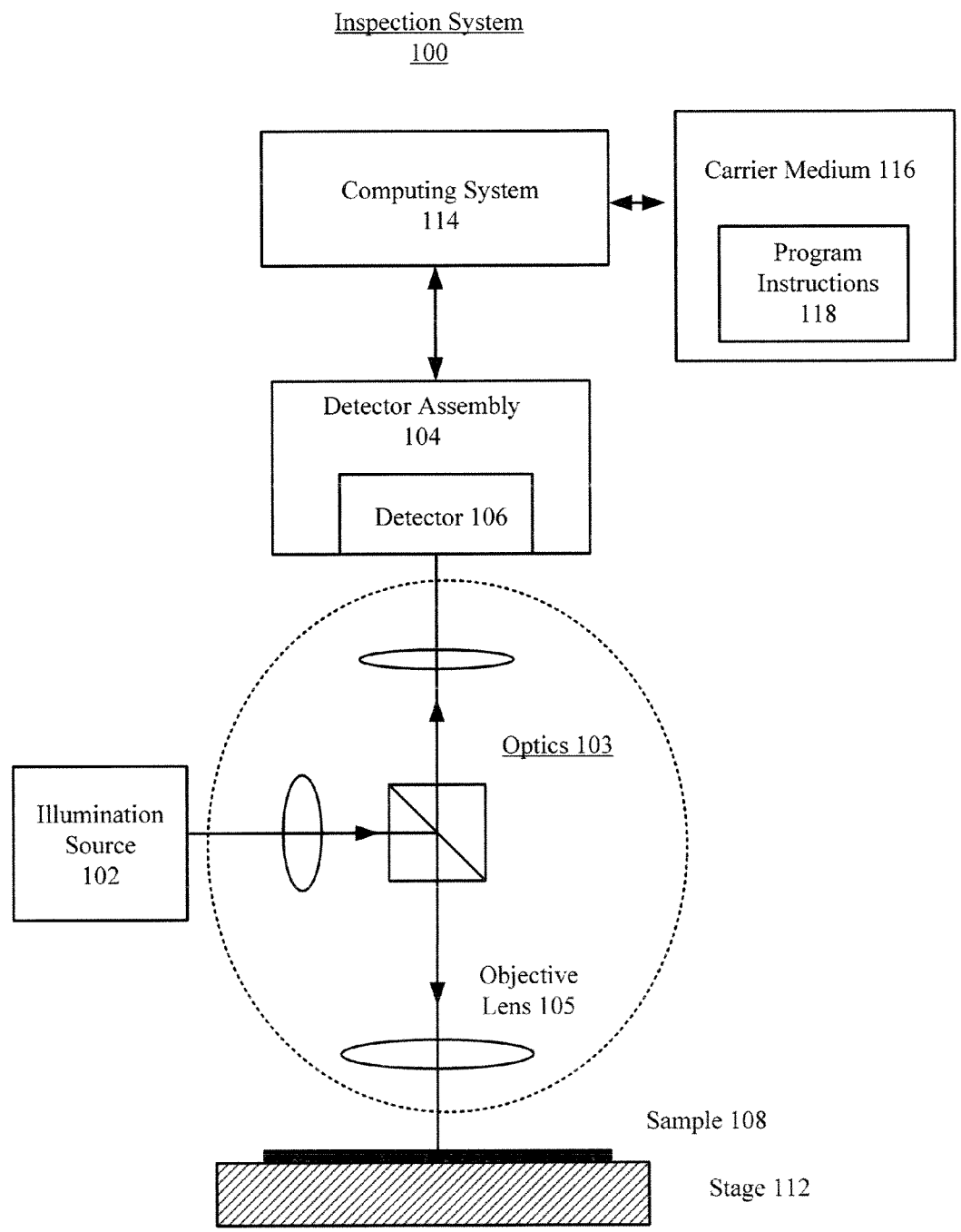
FIG. 1 illustrates an exemplary inspection system incorporating an illumination source that comprises a DUV laser providing optimized bandwidth control.

FIG. 1 illustrates an exemplary inspection system 100 configured to measure a sample 108 such as a wafer, reticle, or photomask. Sample 108 is placed on a stage 112 in order to facilitate movement to different regions of sample 108 underneath the optics. Stage 112 may comprise an X-Y stage or an R-θ stage. In some embodiments, stage 112 can adjust the height of sample 108 during inspection to maintain focus. In other embodiments, an objective lens 105 can be adjusted to maintain focus.

An illumination source 102 may comprise one or more lasers and/or a broad-band light source. Illumination source 102 may emit DUV and/or VUV radiation. Illumination source 102 includes one of the DUV lasers incorporating bandwidth control that is described herein. Optics 103 including an objective lens 105 directs that radiation towards, and focuses it on, sample 108. Optics 103 may also comprise mirrors, lenses, and/or beam splitters. Light reflected or scattered from sample 108 is collected, directed, and focused by optics 103 onto a detector 106, which is within a detector assembly 104. Detector 106 may include a two-dimensional array sensor or a one-dimensional line sensor. In one embodiment, the output of detector 106 is provided to a computing system 114, which analyzes the output. Computing system 114 is configured by program instructions 118, which can be stored on a carrier medium 116.

One embodiment of inspection system 100 illuminates a line on sample 108, and collects scattered and/or reflected light in one or more dark-field and/or bright-field collection channels. In this embodiment, the detector 106 may include a line sensor or an electron-bombarded line sensor.

Another embodiment of inspection system 100 illuminates multiple spots on sample 108, and collects scattered and/or reflected light in one or more dark-field and/or bright-field collection channels. In this embodiment, detector 106 may include a two-dimensional array sensor or an electron-bombarded two-dimensional array sensor.

Additional details of various embodiments of inspection system 100 can be found in U.S. patent application Ser. No. 13/544,954, entitled "Wafer Inspection System", and filed on Jul. 9, 2012, U.S. Pat. No. 7,957,066, entitled "Split Field Inspection System Using Small Catadioptric Objectives", and issued on Jun. 7, 2011, U.S. Pat. No. 7,345,825, entitled "Beam Delivery System For Laser Dark-Field Illumination In A Catadioptric Optical System", and issued on Mar. 18, 2008, U.S. Pat. No. 5,999,310, entitled "Ultra-Broadband UV Microscope Imaging System With Wide Range Zoom Capability", and issued on Dec. 7, 1999, and U.S. Pat. No. 7,525,649, entitled "Surface Inspection System Using Laser Line Illumination With Two Dimensional Imaging", which issued on Apr. 28, 2009. These patents and patent applications are incorporated by reference herein.

Figure 2A:
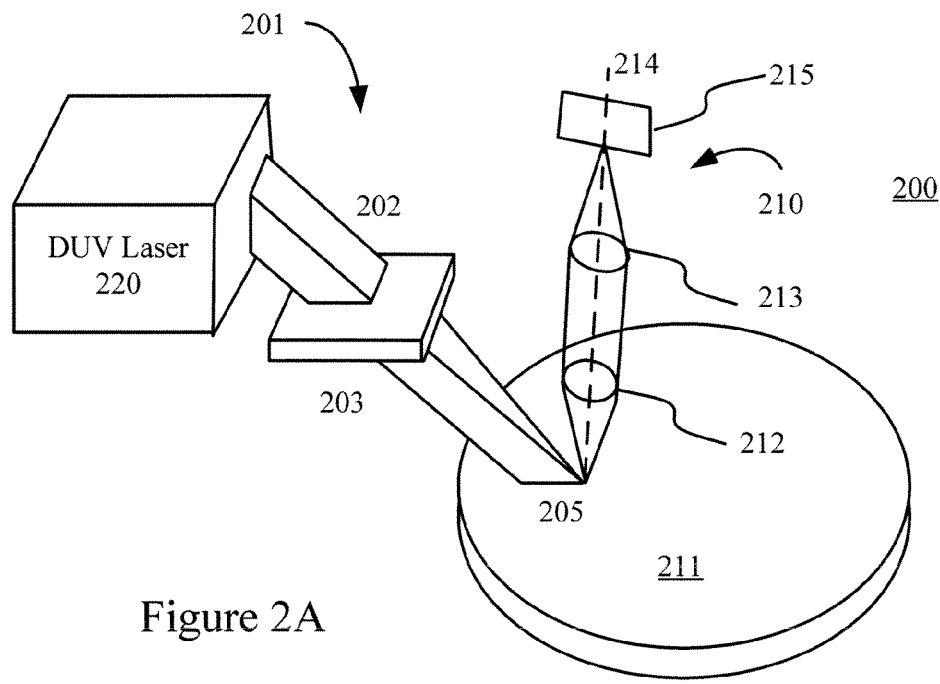
FIGS. 2A and 2B illustrate exemplary inspection systems using line illumination with one, or more, collection channels and a DUV laser providing optimized bandwidth control.
Figure 2B:
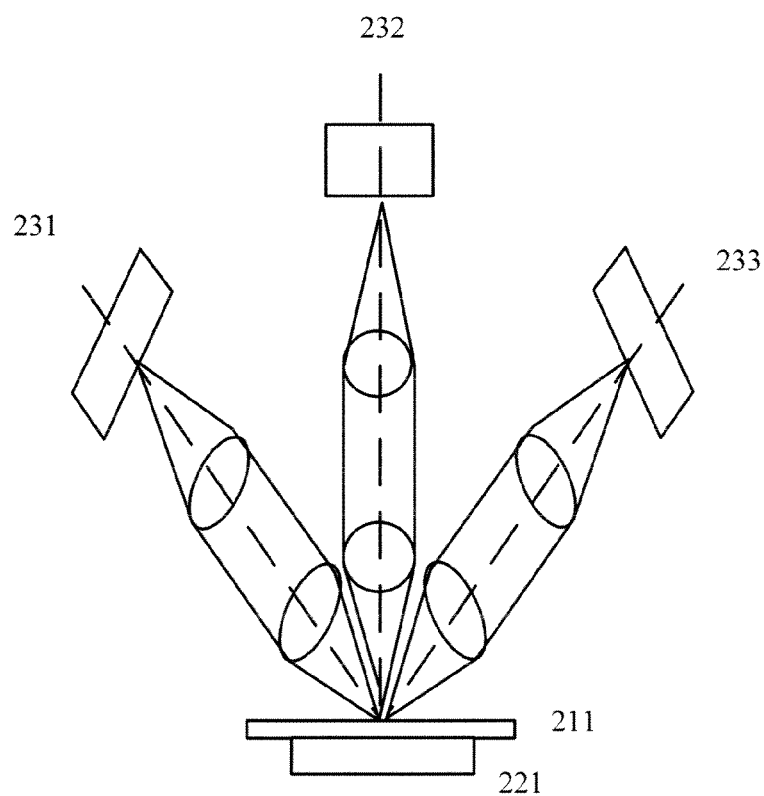

FIGS. 2A and 2B illustrate aspects of dark-field inspection systems that incorporate the DUV lasers and/or methods described herein. For example, in FIG. 2A, illumination optics 201 comprises a DUV laser system 220 for generating light 202 that is focused by a mirror or a lens 203 into a line 205 on the surface of a sample 211 being inspected. DUV laser system 220 includes the DUV laser described herein, which can provide optimized bandwidth control. Collection optics 210 directs light scattered from line 205 to a sensor 215 using lenses and/or mirrors 212 and 213. An optical axis 214 of the collection optics is not in the illumination plane of line 205. In some embodiments, axis 214 is approximately perpendicular to line 205. Sensor 215 may comprise an array sensor, such as a linear array sensor.

FIG. 2B illustrates one embodiment including multiple dark-field collection systems 231, 232 and 233, each system being substantially similar to the collection optics 210 of FIG. 2A. Collection systems 231, 232 and 233 are used in combination with illumination optics substantially similar to illumination optics 201 in FIG. 2A. In this embodiment, sample 211 is supported on a stage 221, which moves the areas to be inspected underneath the optics. Stage 221 may comprise an X-Y stage or an R-θ stage, which preferably moves substantially continuously during the inspection in order to inspect large areas of the sample with minimal dead time.

More details of inspection systems in accordance with the embodiments illustrated in FIGS. 2A and 2B can be found in U.S. Pat. No. 7,525,649, entitled "Surface Inspection System Using Line Illumination With Two Dimensional Imaging", and issued Apr. 28, 2009. U.S. Pat. No. 6,608,676, entitled "System For Detecting Anomalies And/Or Features Of A Surface", and issued Aug. 19, 2003 also describes line illumination systems suitable for inspection of unpatterned or patterned wafers. These patents are incorporated by reference herein.

Figure 3:
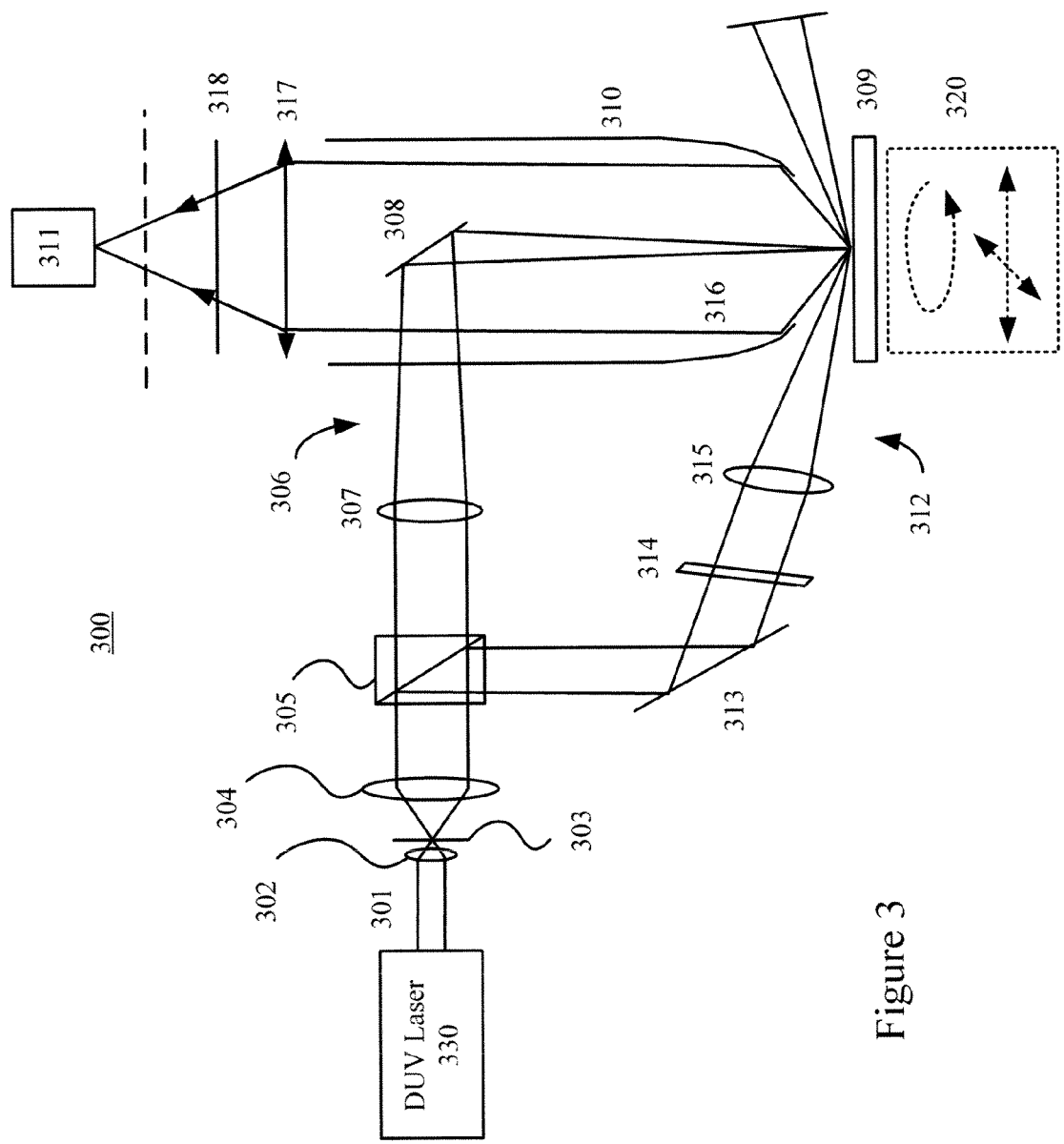
FIG. 3 illustrates an exemplary inspection system including a DUV laser providing normal and oblique illumination as well as optimized bandwidth control

FIG. 3 illustrates an inspection system 300 configured to detect particles or defects on a sample using both normal and oblique illumination beams. In this configuration, a DUV laser system 330 provides a laser beam 301. DUV laser system 330 includes the DUV laser described herein, which provides optimized bandwidth control. A lens 302 focuses the beam 301 through a spatial filter 303. Lens 304 collimates the beam and conveys it to a polarizing beam splitter 305. Beam splitter 305 passes a first polarized component to the normal illumination channel and a second polarized component to the oblique illumination channel, where the first and second components are orthogonal. In the normal illumination channel 306, the first polarized component is focused by optics 307 and reflected by mirror 308 towards a surface of a sample 309. The radiation scattered by sample 309 (such as a wafer or photomask) is collected and focused by a paraboloidal mirror 310 to a sensor 311.

In the oblique illumination channel 312, the second polarized component is reflected by beam splitter 305 to a mirror 313 which reflects such beam through a half-wave plate 314 and focused by optics 315 to sample 309. Radiation originating from the oblique illumination beam in the oblique channel 312 and scattered by sample 309 is also collected by paraboloidal mirror 310 and focused to sensor 311. The sensor and the illuminated area (from both the normal and oblique illumination channels form surface 309) are preferably at the foci of paraboloidal mirror 310.

Paraboloidal mirror 310 collimates the scattered radiation from sample 309 into a collimated beam 316. Collimated beam 316 is then focused by an objective 317 and through an analyzer 318 to sensor 311. Note that curved mirrored surfaces having shapes other than paraboloidal shapes may also be used. An instrument 320 can provide relative motion between the beams and sample 309 so that spots are scanned across the surface of sample 309. U.S. Pat. No. 6,201,601, entitled "Sample Inspection System", and issued on Mar. 13, 2001 describes inspection system 300 in further detail. This patent is incorporated by reference herein.

Figure 4:
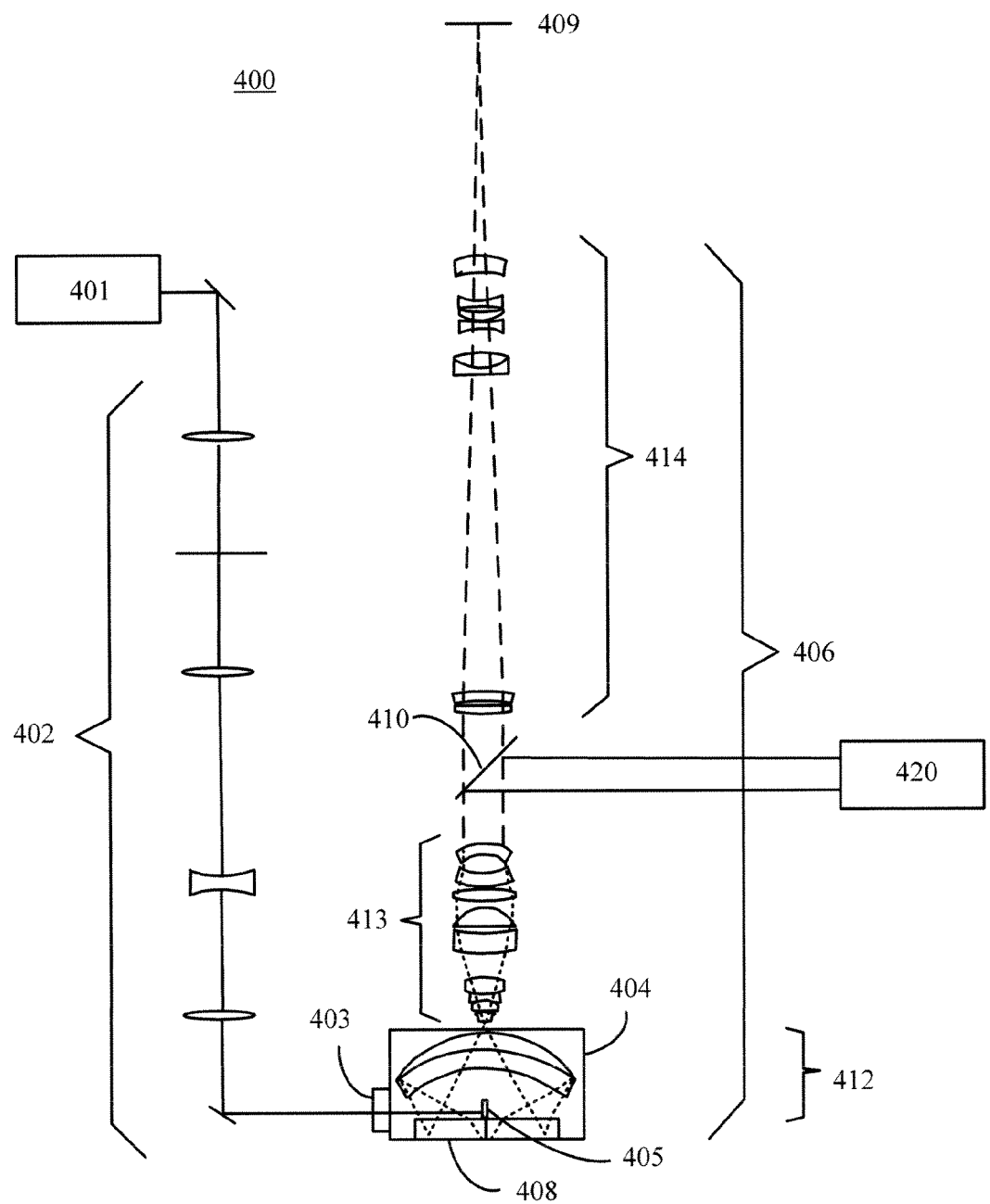
FIG. 4 illustrates an exemplary inspection system with bright-field and dark-field illumination channels. The DUV laser in this inspection system, used for the dark-field illumination channel, provides optimized bandwidth control.

FIG. 4 illustrates an exemplary catadioptric imaging system 400 configured as an inspection system with bright-field and dark-field inspection modes. System 400 may incorporate two illuminations sources: a laser 401, and a broad-band light illumination module 420. In one embodiment, laser 401 may include a DUV laser described herein, which provides optimized bandwidth control.

In a dark-field mode, adaptation optics 402 control the laser illumination beam size and profile on the surface being inspected. Mechanical housing 404 includes an aperture and window 403, and a prism 405 to redirect the laser along the optical axis at normal incidence to the surface of a sample 408. Prism 405 also directs the specular reflection from surface features of sample 408 out of objective 406. Objective 406 collects light scattered by sample 408 and focuses it on a sensor 409. Lenses for objective 406 can be provided in the general form of a catadioptric objective 412, a focusing lens group 413, and a tube lens section 414, which may, optionally, include a zoom capability.

In a bright-field mode, broad-band illumination module 420 directs broad-band light to beam splitter 410, which reflects that light towards focusing lens group 413 and catadioptric objective 412. Catadioptric objective 412 illuminates the sample 408 with the broadband light. Light that is reflected or scattered from sample 408 is collected by objective 406 and focused on sensor 409. Broad-band illumination module 420 comprises, for example, a laser-pumped plasma light source or an arc lamp. Broad-band illumination module 420 may also include an auto-focus system to provide a signal to control the height of sample 408 relative to catadioptric objective 412. U.S. Pat. No. 7,345,825, entitled "Beam Delivery System For Laser Dark-Field Illumination In A Catadioptric Optical System", issued on Mar. 18, 2008, and incorporated by reference herein, describes system 400 in further detail.

Figure 5:
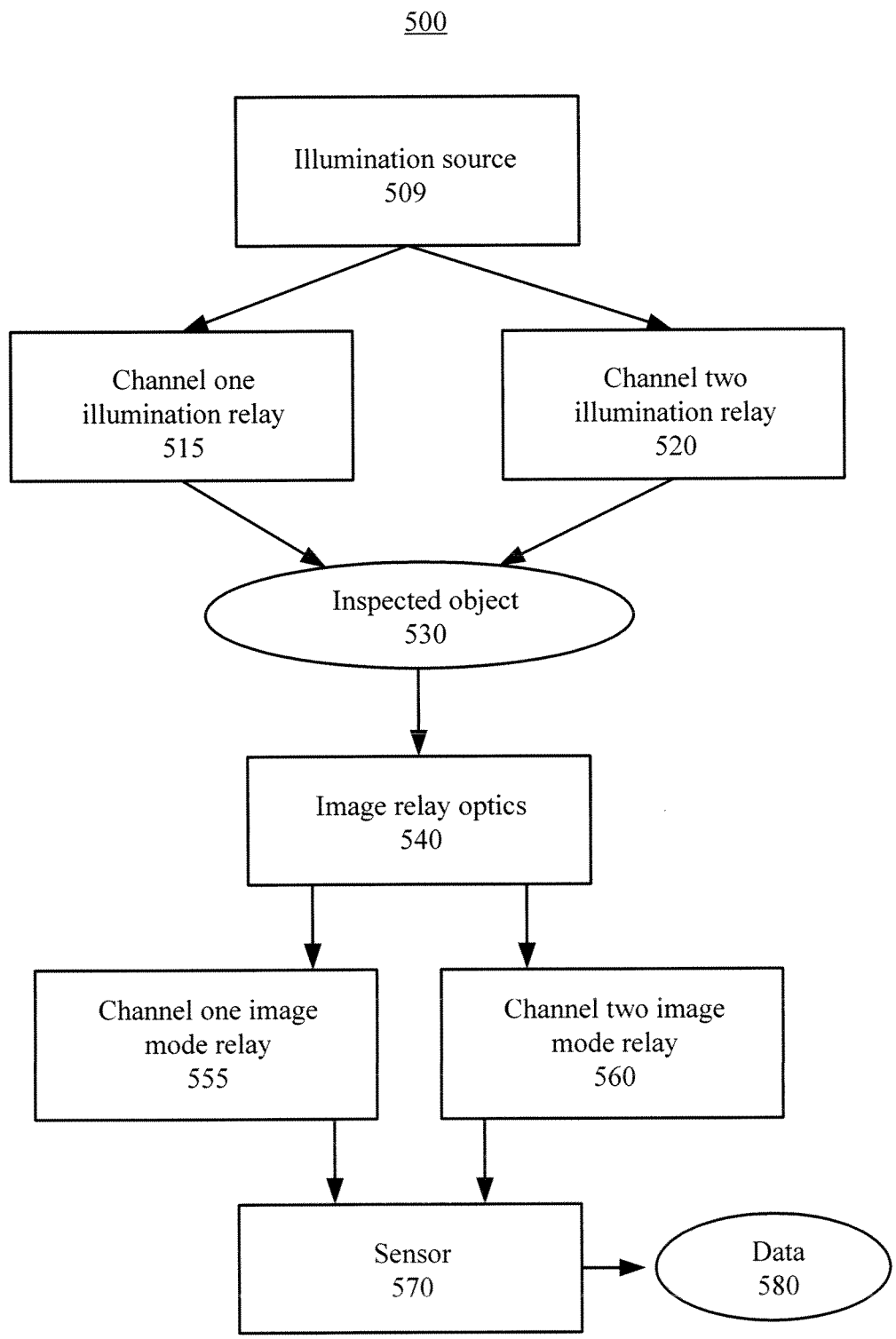
FIG. 5 illustrates an exemplary inspection system incorporating a split-readout image sensor and an illumination source comprising a DUV laser providing optimized bandwidth control.

FIG. 5 illustrates a reticle, photomask, or wafer inspection system 500 that simultaneously detects two channels of image or signal on one sensor 570. Image sensor 570 comprises a split-readout image sensor. Illumination source 509 includes a DUV laser as described herein, which provides optimized bandwidth control. The operating wavelength of this DUV laser may be shorter than 200 nm, such as a wavelength of approximately 193 nm. The two channels may comprise reflected and transmitted intensity when an inspected object 530 is transparent (for example a reticle or photomask), or may comprise two different illumination modes, such as angles of incidence, polarization states, wavelength ranges, or some combination thereof. The light is directed to inspected object 530 using channel one illumination relay 515 as well as channel two illumination relay 520.

Inspected object 530 may be a reticle, a photomask, or a semiconductor wafer to be inspected. Image relay optics 540 can direct the light that is reflected and/or transmitted by inspected object 530 to a channel one image mode relay 555 and to a channel two image mode relay 560. Channel one image mode relay 555 is tuned to detect the reflection or transmission corresponding to channel one illumination relay 515, whereas channel two image mode relay sensor 560 is tuned to detect the reflection or transmission corresponding to channel two illumination relay 520. Channel one image mode relay 555 and channel two image mode relay 560 in turn direct their outputs to a sensor 570. The data corresponding to the detected signals or images for the two channels is shown as data 580 and may be transmitted to a computer (not shown) for processing.

Other details of reticle and photomask inspection systems and methods that may be configured to measure transmitted and reflected light from a reticle or photomask are described in U.S. Pat. No. 7,352,457, entitled "Multiple Beam Inspection Apparatus And Method", issued on Apr. 1, 2008, and in U.S. Pat. No. 5,563,702, entitled "Automated Photomask Inspection Apparatus And Method", issued on Oct. 8, 1996, both of which are incorporated by reference herein.

Figure 6A:
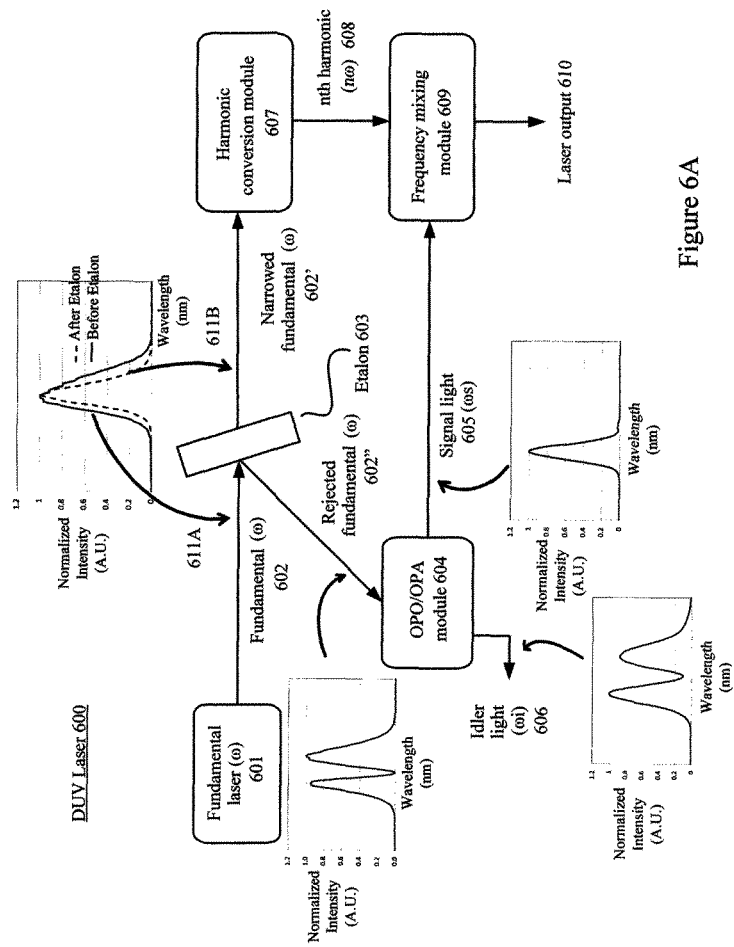
FIG. 6A illustrates an exemplary DUV laser including an optical bandwidth filtering device, e.g. an etalon, to control the bandwidth.

Additional details regarding exemplary embodiments of image sensor 570 are provided in U.S. patent application Ser. No. 14/096,911, entitled "Method And Apparatus For High Speed Acquisition Of Moving Images Using Pulsed Illumination", filed on Dec. 4, 2013, and in U.S. Pat. No. 7,528,943, entitled "Method And Apparatus For Simultaneous High-Speed Acquisition Of Multiple Images", issued May 5, 2009, both of which are incorporated by reference herein FIG. 6A illustrates an exemplary DUV laser 600 configured to provide optimized bandwidth control. An optical parametric oscillator (OPO) or optical parametric amplifier (OPA) 604 is employed in the system. Taking advantage of the wavelength tunability in OPO/OPA 604, DUV laser 600 can generate output light at a chosen specific wavelength, i.e. a wavelength which may or may not be equal to an integer harmonic of the fundamental laser. Notably, the bandwidth of fundamental light 602 (generated by fundamental laser 601) can be narrowed by passing through an etalon 603 (see, e.g. arrows 611A and 611B). Etalon 603 preferably has high transmission over a narrow range of wavelengths centered close to the center wavelength of the fundamental light 602, so that the light transmitted through the etalon, narrowed fundamental 602', has a narrower bandwidth than the fundamental 602. Narrowed fundamental light 602' is directed to a harmonic conversion module 607, which generates an $n^{th}$ harmonic (nω) 608, which is typically a DUV wavelength. Note that the $n^{th}$ harmonic 608 has a narrower bandwidth than would result from providing fundamental 602 to harmonic conversion module 607 directly.

Since etalon 603 reflects most of the incident energy at wavelengths that it does not transmit, as shown in FIG. 6A, an out-of-band rejected fundamental 602" has a broad bandwidth with a dip in the middle of its spectrum. This rejected light 602", which would otherwise be wasted, can be used as a pump light for OPO/OPA 604. As a result of energy conservation in nonlinear parametric process, OPO/OPA 604 can still generate a narrow bandwidth signal light 605 from the broadband pump light of rejected fundamental 602" at the expense of generating a broad bandwidth idler light 606, which has a similar dip in the middle of its spectrum, but a broader bandwidth than rejected fundamental 602". However, because idler light 606 is not used in the laser, this idler light 606 has no significant effect on the laser performance. The bandwidth of signal light 605 is determined by a seed laser or by a wavelength selective element, such as a volume-Bragg grating, in OPO/OPA 604.

In one embodiment, a Raman amplifier can replace OPO/OPA 604. Because the bandwidth of an amplified signal light generated by the Raman amplifier is independent of the bandwidth of its pump light (it typically depends on wavelength selective elements in the Raman amplifier), a Raman amplifier can also generate signal light 605 with a desired narrow bandwidth.

A frequency mixing module 609 can generate a laser output 610 by summing the frequencies of the $n^{th}$ harmonic 608 (nω) and the signal light 605 (ωs). Because the bandwidth of the $n^{th}$ harmonic 608 has been reduced by etalon 603 and the bandwidth of signal light 605 is determined by OPO/OPA 604, the bandwidth of laser output 610 is narrower than it would be in an otherwise identical laser that does not incorporate etalon 603 (that is, bandwidth indicated by arrow 611A would be used instead of bandwidth indicated by arrow 611B). This reduced bandwidth is achieved with minimal power losses since etalon 603 reflects most of the energy that it does not transmit.

In one exemplary embodiment, fundamental laser 601 may operate at a wavelength of approximately 1064 nm using, for example, a Nd:YAG (neodymium-doped yttrium aluminum garnet) or Nd-doped vanadate laser. In this case, harmonic conversion module 607 may generate a fifth harmonic 608 (5ω) of approximately 213 nm, OPO/OPA module 604 may generate signal light 605 having a wavelength of approximately 2108 nm, and frequency mixing module 609 may generate laser output 610 having a wavelength of approximately 193 nm by mixing the 213 nm and 2108 nm wavelengths. The wavelength of approximately 193 nm is a useful wavelength for inspecting semiconductor photomasks and wafers.

In another exemplary embodiment, the fundamental laser 601 may operate at a wavelength of approximately 1064 nm using, for example, a Nd:YAG or Nd-doped vanadate laser. In this case, harmonic conversion module 607 may generate a fourth harmonic 608 (4ω) of approximately 266 nm, OPO/OPA module 604 may generate signal light 605 having a wavelength of approximately 1416 nm, and frequency mixing module 609 first mixes 266 nm and 1416 nm wavelengths to create a sum wavelength of approximately 224 nm, then remixes the sum wavelength of approximately 224 nm with the 1416 nm wavelength signal light 605 to generate a laser output 610 of wavelength approximately 193 nm.

In yet another exemplary embodiment, fundamental laser 601 may operate at a wavelength of approximately 1064 nm using, for example, a Nd:YAG (neodymium-doped yttrium aluminum garnet) or Nd-doped vanadate laser. In this embodiment, harmonic conversion module 607 may generate a fifth harmonic 608 (5ω) of approximately 213 nm, OPO/OPA module 604 may generate signal light 605 having a wavelength of between approximately 1268 nm and approximately 1400 nm, and frequency mixing module 609 may generate laser output 610 having a wavelength of approximately 182.5 nm to approximately 185 nm by mixing the 213 nm and signal wavelengths. The wavelength of approximately 184 nm is a useful wavelength for inspecting semiconductor photomasks and wafers because short wavelengths generally have better sensitivity to smaller features and defects. Furthermore light of approximately 184 nm wavelength can be generated efficiently by this scheme because CLBO is close to non-critically phase matched for such wavelength combinations and so is efficient and stable for the frequency mixing.

Figure 6B:
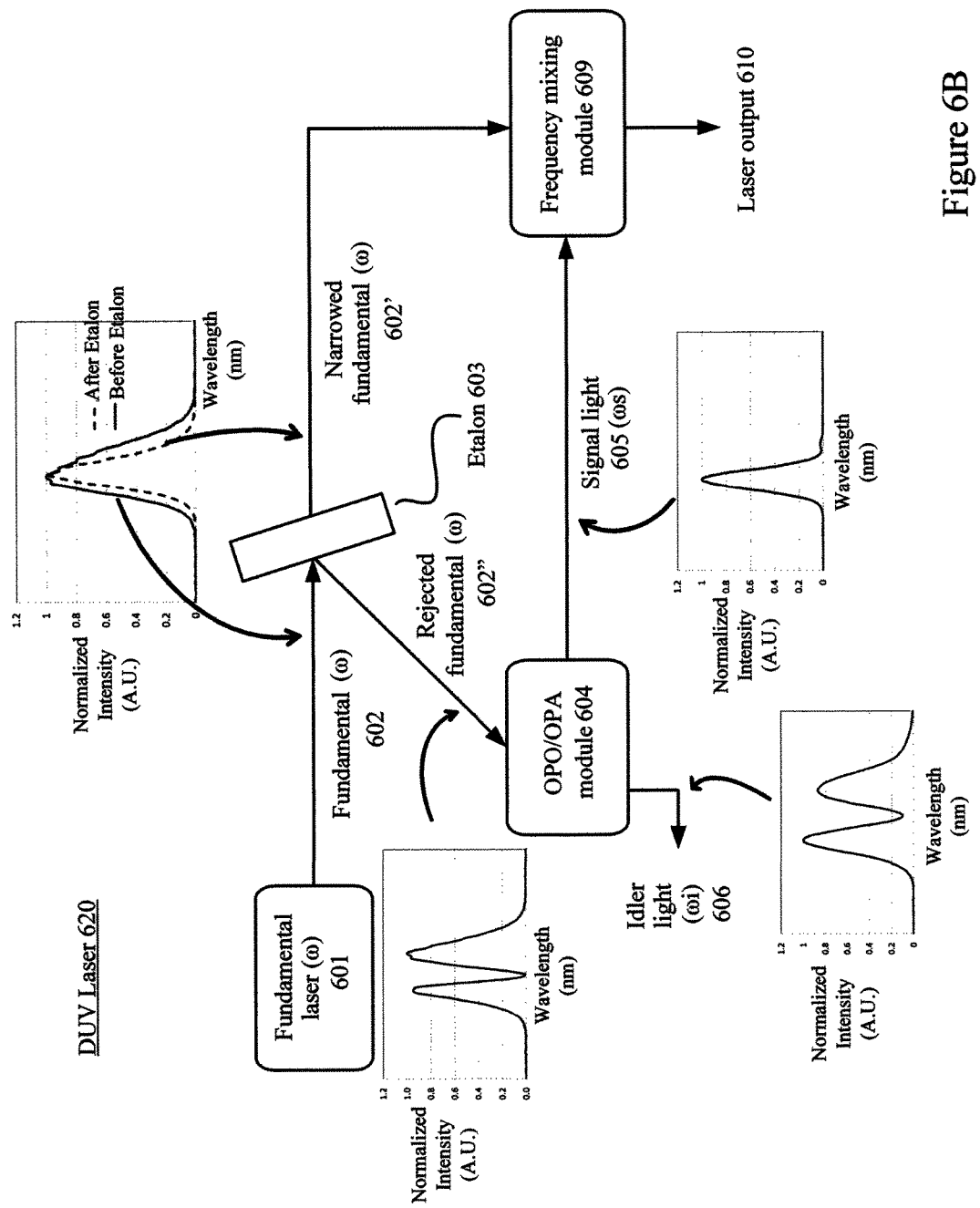
FIG. 6B illustrates an alternate exemplary DUV laser including an optical bandwidth filtering device, e.g. an etalon, to control the bandwidth.

FIG. 6B shows an alternate exemplary DUV laser 620 with optimized bandwidth control. The embodiment of DUV laser 620 is similar to that of DUV laser 600 (FIG. 6A), except that DUV laser 620 does not include a harmonic conversion module. In DUV laser 620, a frequency mixing module 609B generates a laser output 610B by directly mixing narrowed fundamental 602' and signal light 605. Note that components in DUV lasers 620 and 600 having the same labels have the same functions and therefore are not be described in reference to FIG. 6B. DUV laser 620 is particularly useful when fundamental laser 601 generates a UV wavelength, such as a wavelength of 405 nm or 375 nm. Such wavelengths can be generated, for example, by laser diodes.

In one exemplary embodiment, fundamental laser 601 may comprise a laser diode operating at a wavelength of approximately 375 nm. In this case, OPO/OPA module 604 may generate signal light 605 having a wavelength of between approximately 607 nm and approximately 750 nm, and frequency mixing module 609 may generate laser output 610 having a wavelength of between approximately 232 nm and approximately 250 nm by mixing the 375 nm and signal wavelengths. This scheme can efficiently and inexpensively generate the output wavelength of between approximately 232 nm and approximately 250 nm because frequency mixing module 609 may use a CLBO crystal for frequency mixing. CLBO is close to non-critically phase matched for such wavelength combinations and so can do the frequency mixing efficiently and stably.

Figure 6C:
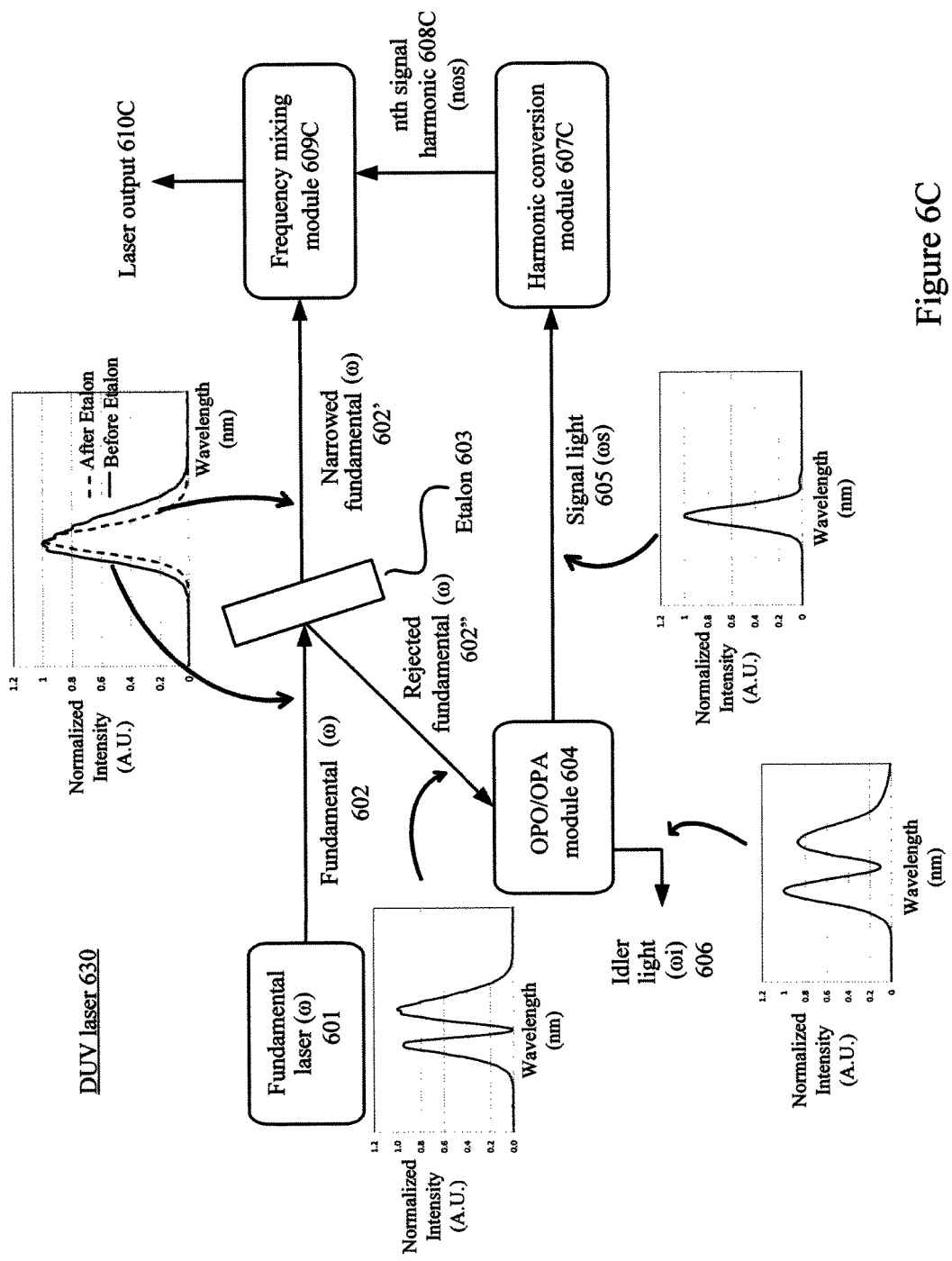
FIG. 6C illustrates another exemplary DUV laser including an optical bandwidth filtering device, e.g. an etalon, to control the bandwidth.

FIG. 6C shows another exemplary DUV laser 630 with optimized bandwidth control. This embodiment of DUV laser 630 is similar to that of DUV laser 600 (FIG. 6A), with the following exceptions. In this case, a harmonic conversion module 607C is used to generate an $n^{th}$ signal harmonic 608C (n$\omega$s) of signal light 605. Additionally, a frequency mixing module 609C generates a laser output 610C by mixing narrowed fundamental 602' and $n^{th}$ signal harmonic 608C. Note that components in DUV lasers 630 and 600 having the same labels have the same functions and therefore are not be described in reference to FIG. 6C. The embodiment of DUV 630 is particularly useful when the wavelength of laser output 610C cannot be achieved with a specific fundamental laser (for example, because the available non-linear crystals for frequency mixing module 609 or harmonic conversion module 607 (DUV laser 600, FIG. 6A) cannot phase match for one or more of the wavelengths). DUV laser 630 can provide different wavelength combinations for frequency mixing module 609C and harmonic conversion module 607C and can, in some cases, provide a viable way to generate the desired laser output wavelength when the embodiment of DUV 600 (FIG. 6A) cannot.

In one exemplary embodiment, fundamental laser 601 may operate at a wavelength of approximately 800 nm using, for example, a Ti-sapphire laser. In this case, OPO/OPA module 604 may generate signal light 605 ($\omega$s) having a wavelength between approximately 888 nm and 1080 nm, harmonic conversion module 607 may generate a third harmonic 608 (3$\omega$s) of between approximately 296 nm and 360 nm, and frequency mixing module 609 may generate laser output 610 having a wavelength of between approximately 216 nm and 248 nm by mixing the third harmonic and the approximately 800 nm wavelengths.

Figure 7:
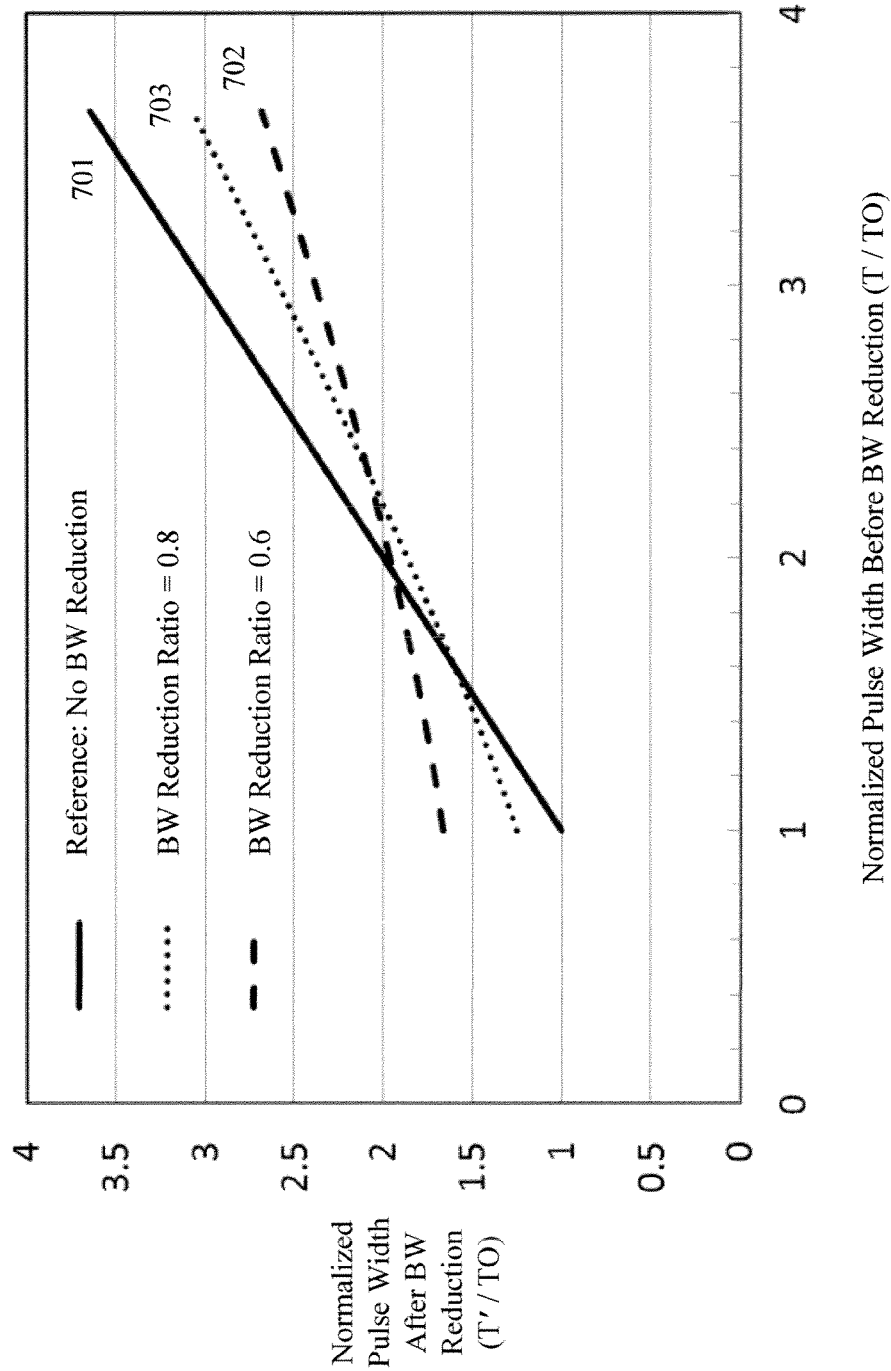
FIG. 7 illustrates an exemplary pulse width shortening after bandwidth filtering.

FIG. 7 illustrates how pulse width shortening is possible by bandwidth filtering. Laser pulses generated by mode-locked or modulated laser oscillators usually have approximately Gaussian spectral shapes and exhibit approximately linear chirp. "T0" is the transform-limited pulse width of a pulse with the same bandwidth as the chirped pulse; "T" is the pulse width before bandwidth reduction; and "T'" is the pulse width after bandwidth reduction. A bandwidth reduction ratio is defined as the pulse bandwidth after filtering (i.e. after passing through the etalon) divided by the pulse bandwidth before filtering. In FIG. 7, the case without bandwidth reduction, i.e. T'=T, is plotted as a solid line 701 for reference. Points above line 701 represent cases where the pulse width increases, i.e. T'>T. Points below line 701 represent cases where the pulse width decreases, i.e. T'<T. Two cases of different bandwidth reduction ratios (0.6 and 0.8) are illustrated by dashed line 702 and dotted line 703 respectively.

FIG. 7 shows that under certain circumstances, bandwidth reduction of a chirped pulse would result in a shorter pulse, which is closer to transform-limited. For example, for the 0.6 bandwidth reduction ratio, when the pulse width T is greater than about 2 T0, reducing the bandwidth shortens the pulse width. In another example, for the 0.8 bandwidth reduction ratio, when the pulse width T is greater than about 1.6 T0, the pulse width is reduced when the bandwidth is reduced. As explained above, reducing the pulse width helps maintain the efficiency of the harmonic conversion and frequency mixing processes. Note that when the initial pulse width is close to T0, i.e. the initial pulse is close to transform limited, then any bandwidth reduction necessarily increases the pulse width.

The lines plotted in FIG. 7 were calculated for Gaussian pulse shapes. Other common laser pulse shapes such as sech$^2$ pulses show the same trends. See, for example, Agrawal, "Nonlinear Fiber Optics", 4th ed, pp 54-59, Academic Press, 2007.

A typical high powered laser (such as a laser with an output of about 30 W or more) has a pulse width significantly longer than a transform-limited pulse of the same bandwidth. As a result, the various methods and DUV lasers disclosed herein are particularly useful for generating narrow bandwidth DUV laser output light at powers of about 100 mW or more while maintaining good conversion efficiency.

More detailed descriptions of 193 nm lasers that can benefit from the optimized bandwidth control of the DUV lasers described herein are provided by U.S. patent application Ser. No. 13/797,939, entitled "Solid-state 193 nm laser and an inspection system using a solid-state 193 nm laser", and filed on Mar. 12, 2013, U.S. Provisional Patent Application 61/756,209, entitled "193 nm laser using OPO and an inspection system using a 193 nm laser", and filed on Jan. 24, 2013, and U.S. Provisional Patent Application 61/764,441, entitled "193 nm laser using 1109 nm", and filed on Feb. 13, 2013. All of these applications are incorporated by reference herein.

Note that the above-described DUV lasers can be operated at other wavelengths shorter than about 200 nm by appropriate selection of the wavelength of the signal light $\omega$s and appropriate changes to the frequency mixing module (i.e. frequency mixing modules 609, 609B or 609C). In particular, vacuum UV wavelengths shorter than 190 nm can be generated by such lasers.

Exemplary embodiments of image sensors suitable for use in an inspection or imaging system incorporating any of the DUV lasers described herein can be found in U.S. Published Patent Application 2013/0264481, entitled "Back-Illuminated Sensor With Boron Layer", which published on Oct. 10, 2013 and is incorporated by reference herein.

The above description is presented to enable one of ordinary skill in the art to make and use the invention as provided in the context of a particular application and its requirements. As used herein, directional terms such as "top", "bottom", "over", "under", "upper", "upward", "lower", "down" and "downward" are intended to provide relative positions for purposes of description, and are not intended to designate an absolute frame of reference. The various embodiments of the DUV laser having optimized bandwidth control and methods described above are illustrative only and are not intended to limit the scope of the invention.

Various modifications to the described embodiments will be apparent to those with skill in the art, and the general principles defined herein may be applied to other embodiments. For example, the harmonic conversion modules 607 of FIG. 6A and 607C of FIG. 6C might generate a second, third, fourth, fifth, sixth or higher harmonic. In another example, an etalon or interferometer may be designed to reflect a narrow range of wavelengths and transmit wavelengths outside that narrow range. Such an optical bandwidth filtering device could be substituted for the etalon 603 of FIGS. 6A, 6B and 6C with an appropriate change of the layout of the laser. The narrowed fundamental 602' would be reflected to harmonic conversion module 607, frequency mixing module 609 or frequency mixing module 609C as appropriate, and the rejected fundamental 602" would be transmitted to the frequency conversion module such as OPO/OPA 604.

Therefore, the DUV lasers and methods described herein are not intended to be limited to the particular embodiments shown and described, but are to be accorded the widest scope consistent with the principles and novel features herein disclosed.

The invention claimed is:

1. A laser comprising:
a fundamental laser configured to generate a fundamental wavelength with a fundamental wavelength bandwidth;
a frequency conversion module configured to receive a first portion of the fundamental wavelength and to use the first portion as pump light to generate a second wavelength;
a harmonic conversion module configured to generate a harmonic wavelength by converting a second portion of the fundamental wavelength;
a frequency mixing module configured to mix the second wavelength with the harmonic wavelength to generate a sum wavelength shorter than 200 nm; and
an optical bandwidth filtering device positioned to receive the fundamental wavelength from the fundamental laser and configured to generate the first portion and the second portion from the fundamental wavelength such that the second portion comprises a narrower range of wavelengths within the fundamental wavelength bandwidth than the first portion.

2. The laser of claim 1, wherein the optical bandwidth filtering device is positioned outside a laser oscillator cavity.

3. The laser of claim 1, wherein the optical bandwidth filtering device includes at least one device selected from a group consisting of an etalon, an optical dielectric filter, a volume Bragg grating, a birefringence filter, and an optical grating.

4. The laser of claim 1, wherein the frequency conversion module includes at least one device selected from a group consisting of an optical parametric oscillator (OPO), an optical parametric amplifier (OPA), and a Raman amplifier.

5. The laser of claim 4, wherein the second wavelength is generated as signal light from the OPO or the OPA.

6. The laser of claim 5, wherein the fundamental laser comprises a fiber laser, a neodymium-doped yttrium aluminum garnet (Nd:YAG) laser, or a Nd-doped vanadate laser.

7. The laser of claim 6, wherein the sum wavelength is a wavelength between about 180 nm and 200 nm.

8. A method of generating deep UV laser radiation, the method comprising:
generating a fundamental laser light having a fundamental wavelength and a fundamental wavelength bandwidth;
separating the fundamental laser light into a first portion and a second portion such that the second portion comprises a narrower range of wavelengths within the fundamental wavelength bandwidth than the first portion;
using the first portion as pump light to generate a second wavelength;
generating a harmonic wavelength by converting the second portion; and
summing the second wavelength and the harmonic wavelength to generate a deep UV output wavelength.

9. The method of claim 8, wherein said separating comprises positioning at least one of an etalon, an optical dielectric filter, a volume Bragg grating, a birefringence filter or an optical grating to receive the fundamental laser light.

10. The method of claim 8, wherein said converting the first portion to the second wavelength is performed by an OPO, an OPA, or a Raman amplifier.

11. The method of claim 8, wherein said generating the fundamental laser light is performed by one of a Nd:YAG laser, an Nd-doped vanadate laser, and an Yb-doped fiber laser.

12. The method of claim 11, wherein the output wavelength is wavelength between approximately 180 nm and 200 nm.

* * * * *